(12) United States Patent
Wallace et al.

(10) Patent No.: US 7,534,596 B2
(45) Date of Patent: May 19, 2009

(54) METHOD AND DEVICE FOR PRODUCING VACCINE

(75) Inventors: Bonnie L. Wallace, Ann Arbor, MI (US); William J. Hillegas, Ann Arbor, MI (US)

(73) Assignee: Solohill Engineering, Inc., Ann Arbor, MI (US)

( * ) Notice: Subject to any disclaimer, the term of this patent is extended or adjusted under 35 U.S.C. 154(b) by 0 days.

(21) Appl. No.: 11/705,920

(22) Filed: Feb. 12, 2007

(65) Prior Publication Data

US 2007/0202527 A1    Aug. 30, 2007

Related U.S. Application Data

(60) Provisional application No. 60/772,156, filed on Feb. 10, 2006.

(51) Int. Cl.
*C12N 7/00*    (2006.01)
*A61K 39/145*    (2006.01)
*A61K 39/38*    (2006.01)
*C12Q 1/70*    (2006.01)

(52) U.S. Cl. ............... 435/235.1; 424/184.1; 424/206.1; 424/209.1; 435/5

(58) Field of Classification Search ................ None
See application file for complete search history.

(56) References Cited

U.S. PATENT DOCUMENTS 6,656,719 B1*    12/2003    Gould et al. ............. 435/235.1
2004/0265987 A1*    12/2004    Trager et al. ................ 435/239

OTHER PUBLICATIONS

White and Ades. Growth of Vero E-6 Cells on Microcarriers in a Cell Bioreactor. Journal of Clinical Microbiology, 1990; 28(2): 283-286.*
SoloHill Microcarrier Reference Guide. Updated Nov. 1, 2005.*

* cited by examiner

*Primary Examiner*—Mary E Mosher
*Assistant Examiner*—Stuart W Snyder
(74) *Attorney, Agent, or Firm*—Kohn & Associates, PLLC

(57) ABSTRACT

A method of making a vaccine using animal derived component free (ADCF) cell culture technology, including the steps of attaching ADCF-adapted cells to a microcarrier including an attachment mechanism for attaching filipodia of the cells, the microcarrier being in a culture, growing the cells in ADCF maintenance media, infecting the cells with vaccine media, producing virus within the cells, and harvesting the virus. A vaccine produced by the above method in a pharmaceutically acceptable carrier. A vaccine production structure of ADCF-adapted cells removably attached to microcarrier beads including an attachment mechanism for attaching filipodia of the cells.

17 Claims, 8 Drawing Sheets

METHOD AND DEVICE FOR PRODUCING VACCINE

CROSS-REFERENCE TO RELATED APPLICATIONS

This application claims the benefit of priority under 35 U.S.C. Section 119(e) of U.S. Provisional Patent Application No. 60/772,156, filed Feb. 10, 2006, which is incorporated herein by reference.

BACKGROUND OF THE INVENTION

1. Technical Field

The present invention relates to a method and device for producing a vaccine. More specifically, the present invention relates to a protein-free cell culture process for producing a vaccine.

2. Description of the Related Art

Immunization to protect against communicable disease is one of the most successful and cost-effective practices of modern medicine. Smallpox has been completely eliminated by vaccination, and the incidence of many other dreaded diseases such as polio and diphtheria has been drastically reduced through immunization programs. However, vaccines, especially those based on the use of inactivated viruses, vary in effectiveness. For example, while the currently licensed influenza vaccine is reportedly over 80% efficacious in young adults, it is only approximately 60% efficacious in adults 65 years of age and older, and less than 50% effective in children under 2 years of age. The recently licensed chicken pox vaccine is reportedly approximately 70% efficacious, and there are currently no effective vaccines against many important viral diseases including those caused by respiratory syncytial virus, parainfluenza 3 virus, Rotavirus, and the human immunodeficiency virus. In some cases, licensed inactivated viral vaccines may cause adverse reactions that have prevented their use at the higher dosages needed to improve efficacy.

Inactivated virus vaccines confer protection by stimulating immune responses to proteins found in the free virus. Antibodies to the mature envelope proteins found on free virus may be optimal in blocking the initial events of infection (such as virus binding to a cell receptor and attachment and entry into a cell) following exposure to a virus, but may be sub-optimal once a virus has entered a cell. Once infected, the cells and the cell-associated immature virions contain precursors to the mature envelope proteins. These precursor proteins may stimulate more optimal immune responses for stemming the spread of infection and preventing clinical illness when the body's first line of defense, antibodies to free virus, does not completely prevent all viruses from infecting cells.

Inactivated virus vaccines are typically produced from virus that has been grown in animal cells, e.g. embryonated eggs for influenza, which are then inactivated by treatment with chemicals such as formalin. Attenuated vaccines for measles and chickenpox are produced by growing weakened virus in cell cultures. Advances in the understanding of the pathogenesis of viral infections and recombinant DNA technology have led to the identification and production of specific viral proteins for use in subunit viral vaccines. These have been particularly successful in the formulation of a subunit vaccine against the hepatitis B virus.

Most existing licensed vaccines and vaccines in development, whether based on inactivated viruses or recombinant DNA technology, rely primarily on immune responses to the mature virus, or, in a few examples of experimental, recombinant DNA-based vaccines, immune responses to antigens found in the cell-associated form of the virus, or virus-infected cells. Both the killed virus and attenuated virus approaches on the one hand and the recombinant DNA approaches on the other hand have their advantages and their limitations. While the cell culture and embryonated egg methods are used to grow whole virus very inexpensively, they are not very efficient methods for the commercial production of the viral precursor proteins found in the infected cells and the cell-associated forms of the virus. This is because these methods act like miniature assembly lines and, while a large amount of mature virus accumulates in the cell cultures or the eggs at any given time, a much smaller amount of virus is actually in the process of being assembled. Therefore, the purified virus used to make the vaccine contains very little, if any, of the envelope precursor or other precursor proteins. On the other hand, viral membrane glycoproteins, in either their mature or precursor form, can be efficiently produced by recombinant DNA technology. When native conformational structure is needed to produce functional, neutralizing antibodies, the use of recombinant technology employing mammalian cell or insect cell substrates is preferred. However, production of viral vaccine proteins in insect or mammalian cells by recombinant methods is generally more expensive on a per milligram protein basis than cell culture and egg production methods.

Adverse reactions from vaccines may arise from impurities or from biologic properties of the vaccine proteins (antigens) responsible for conferring protective immunity. For example, the contaminating egg protein present in the licensed influenza vaccines may be largely responsible for the adverse reactions associated with these products.

Mature viral proteins present in vaccines may have biologic properties that are responsible for adverse reactions. Uptake by mononuclear cells and granulocytes of inactivated influenza virus mediated by the mature hemagglutinin may also be responsible for adverse reactions. The mature HIV envelope glycoprotein (gp120) in some experimental vaccines against HIV may bind to the CD4 receptor of T4 lymphocytes and alter normal immune function. It would be desirable to reduce potential adverse reactions in the vaccine preparations.

The viral envelope proteins in inactivated virus vaccines are substantially glycosylated. While glycosylation is important in maintaining conformational structure of these proteins it may also reduce their immunogenicity. These proteins in either the mature of precursor form can be produced with trimmed carbohydrate residues with recombinant baculovirus expression vectors and insect cells. The baculovirus-produced proteins retain sufficient native conformation to stimulate functional neutralizing antibodies and may provide greater immunogenicity than highly glycosylated native proteins.

Infection by influenza virus causes substantial illness and premature death worldwide. Immunization with vaccines comprised of preparations of inactivated influenza viruses is currently the most useful practice for reducing disease from viral influenza. The vaccines confer protection against infection and disease by stimulating the production of immune responses to the hemagglutinin (HA), neuraminidase (NA), nucleoproteins (NP, M1) and possibly other proteins of component strains (Murphy, B. R., et al., N. Engl. J. Med. 268: 1329-1332 (1972) and Kendal, A. P., et al., J. Infect. Dis. 136:S415-24 (1986)). The most important of these is the production of neutralizing antibodies to HA (Ada, G. L., and Jones, P. D., Curr. Top. Microbiol. Immunol. 128:1-54 (1986)). The currently available inactivated vaccines nevertheless have limitations, including sub-optimal immunogenicity and efficacy in adults 65 years of age and older and very young children and under utilization in part due to poor patient acceptance in connection with the belief that such vaccines are not very effective and fears of adverse reactions (Nichol, K. L., et al., Arch. Int. Med. 152:106-110 (1992)). The perception of lack of effectiveness arises in part from variations in potency from year to year and the association of many non-influenza respiratory tract illnesses with influenza.

The mature influenza virus contains both HA and NA proteins in its outer envelope. The HA is present as trimers. Each HA monomer consists of two polypeptides (HA1 and HA2) linked by a disulfide bond. These polypeptides are derived by cleavage of a single precursor protein, HA0, during maturation of the influenza virus. In part, because these molecules are tightly folded, the HA0 and the mature HA1 and HA2 differ slightly in their conformation and antigenic characteristics. Furthermore, the HA0 is more stable and resistant to denaturation and to proteolysis. Recently it has been reported that a baculovirus/insect cell culture derived recombinant HA0 conferred protective immunity to influenza (Wilkinson, B., MicroGeneSys Recombinant Influenza Vaccine, PMA/CBER Viral Influenza Meeting, Dec. 8, 1994). One limitation of recombinant HA0 vaccines is their inability to stimulate immune responses against non-HA antigens that may provide greater and more durable protection, especially for high-risk populations that do not respond well to immunization.

Current production of human influenza vaccine takes place primarily in fertile chicken eggs. Worldwide several hundred million of eggs are used each year to produce vaccine for the influenza season. The current production cycle (beginning with identification of the anticipated virus strains expected to be present in the forthcoming influenza season) is many months long. The current production processes that use fertile eggs as tiny bioreactors is labor intensive, expensive and fraught with variables, such as the seasonal availability and variation of properties of the eggs.

It would therefore be desirable to provide improved virus vaccine preparations that do not exhibit as many of the limitations and drawbacks observed with the use of currently available vaccines.

BRIEF SUMMARY OF THE INVENTION

The present invention provides a method of making a vaccine using animal derived component free (ADCF) cell culture technology by attaching ADCF-adapted cells to a microcarrier including an attachment mechanism for attaching filipodia of the cells, the microcarrier being in a culture, growing the cells in ADCF maintenance media, infecting the cells with vaccine media, producing virus within the cells, and harvesting the virus.

The present invention further provides a vaccine produced by the above method in a pharmaceutically acceptable carrier.

The present invention also provides a vaccine production structure of ADCF-adapted cells removably attached to microcarrier beads including an attachment mechanism for attaching filipodia of the cells.

BRIEF DESCRIPTION OF THE SEVERAL VIEWS OF THE DRAWINGS

Other advantages of the present invention will be readily appreciated as the same becomes better understood by reference to the following detailed description when considered in connection with the accompanying drawings wherein:

FIG. 1 is a photograph of synchronized, evenly distributed cell attachment to HILLEX® (SoloHill Engineering, Inc.) II, the impeller is on until cell attachment is achieved, typically within 30 minutes;

FIG. 2 shows Vero cells spreading (white) on HILLEX® within 24 hours during intermittent stirring;

FIG. 3 shows Vero cells growing (white) on HILLEX® after 72 hours in culture;

FIG. 4 shows confluent Vero ADCF cells on HILLEX® after 4 days in culture;

FIG. 5 shows growth curve; x axis hours in culture and y axis number of cells;

FIG. 6 shows cells properly maintained with ADCF DMEM prior to infection;

FIG. 7 shows cells improperly maintained with ADCF growth media resulting in cells slough off microcarriers; and FIG. 8 shows a comparison of A/Panama H3N2 harvest titer.

DETAILED DESCRIPTION OF THE INVENTION

The present invention provides a method of making a vaccine using microcarrier beads. Specifically, the a vaccine is made using animal derived component free (ADCF) cell culture technology by attaching ADCF-adapted cells to a microcarrier including an attachment mechanism for attaching filipodia of the cells, the microcarrier being in a culture, growing the cells in ADCF maintenance media, infecting the cells with vaccine media, producing virus within the cells, and harvesting the virus. This method utilizes microcarrier bead technology to develop vaccines via the methodology disclosed in the examples. The vaccines developed are any vaccine that can be produced in the manner disclosed herein. Further, the method of the present invention can be used to develop new vaccines. The present invention also provides a vaccine production structure of the ADCF-adapted cells which are removably attached to the microcarrier beads as described above and further detailed below.

The present invention utilizes microcarrier beads which have an attachment mechanism of a micro-porous surface. This micro-porous surface provides stronger attachment of cells to the microcarrier bead through the extension of filipodia from the cells. The preferred microcarrier bead has a density in the range of 1.04 to 1.1 g/cc. Additional sized beads or beads made of heavier material are suited for certain applications.

A number of different materials including glass, polystyrene plastic, acrylamide, solid collagen, porous collagen, cellulose and liquid fluorocarbons have been successfully used as microcarriers (Varani, et al. (1983); Nielson, et al. (1980); Obrenovitch, et al. (1982); Giard, et al., (1977); Gebb, et al., (1982)). In addition, microcarriers with one or more adhesive peptides attached to the surface through covalent or noncovalent linkages have been used (Keese, et al. (1983); Varani, et al. (1988); Varani, et al., (1986)). To be useful as a microcarrier, a material must have a surface chemistry which supports cell attachment and growth, and must not be toxic to the cells or to the elaborated products. The ideal microcarrier has a diameter of approximately 75-225 μm, although larger or smaller sizes (U.S. Pat. No. 5,114,855 (May 1992); J. Varani, S. Josephs and W. Hillegas, "Human Diploid Fibroblast growth in polystyrene microcarriers in aggregates", Cytotechnology, 22: 111-117 (1996)) have been used.

Two types of microcarrier products are widely-used in the industry today. These are the i) dextran-based microcarriers (Cytodex. I, DEAE-dextran; and Cytodex III, porcine collagen-coated dextran) made in Sweden and sold by Amersham-Pharmacia Biotech of the United Kingdom and ii) the coated polystyrene based microcarriers made in the United States by SoloHill. Microcarriers made by SoloHill have been successfully integrated into manufacturing processes in the United States, Europe and Japan. SoloHill makes a porcine collagen-coated polystyrene microcarrier bead, which is heavily used in the animal health industry to produce viral vaccines. Smaller amounts of Solohill's glass-coated polystyrene microcarriers have also found a use in industry, and an intense interest has developed in the recently-released ProNectin F*—coated polystyrene beads, largely because they are free of animal proteins. *ProNectin F is a genetically engineered protein incorporating multiple copies of the cell attachment ligand (RGD) from fibronectin. The microcarrier bead made with a t-butyl styrene core can be further coated if important to cell culture. This coating can include, but is not limited to porcine, bovine or human collagen, or ProNectin F, a recombinant fibronectin, or other natural or synthetic peptides. This coating is applied in the same manner as is utilized for standard collagen-coated polystyrene microcarriers. (See U.S. Pat. No. 4,944,388 to Hillegas, et al.).

The examples below detail the protocols used for making influenza vaccine using animal derived component free (ADCF) cell culture technology. Cell culture technology presents the advantages of automation through large batch, computer controlled bioreactors, and thus a highly reproducible manufacturing protocol. The uniqueness of this invention is that this process; (a) uses adapted mammalian cells such as Vero or Madin-Darby Canine Kidney (MDCK) cells, (b) uses media formulations that contain no animal derived components, (c) uses microcarriers such as the protein-free types developed, produced and sold by SoloHill and (d) is developed for commercial-scale manufacturing using computer controlled bioreactors capable of producing batches of high-titer vaccine of 1,000 liters or even larger. An added advantage to this cell culture process compared to the conventional egg-based technology is the rapid turnaround time when an influenza pandemic arises. Thus the described cell-culture based technology is vastly more capable of producing appropriate vaccine to counteract an outbreak of a monovalent virus.

Vero cells, adapted to animal derived component free (ADCF), HILLEX® II microcarrier culture conditions infected with various strains of influenza virus generate high virus yields and exemplify the ADCF upstream process described in this application. Critical steps identified for the ADCF process for influenza production include 1) robust ADCF-adapted cell line, 2) removal of cells from substrate using ADCF trypsin resulting in a single cell suspension for culture initiation, 3) uniform cell attachment to HILLEX® II microcarrier, 4) timely cell spreading to HILLEX® II microcarrier following attachment, 5) cell growth as a function of ADCF media management, 6) maintenance of robust cells prior to influenza infection using ADCF maintenance media, 7) Vero cell adapted influenza virus working seeds with adequate titers to infect the cell cultures, and 8) timing of cell infection relative to cell seeding density on HILLEX® II microcarrier and growth phase of the cells where all factors synergistically produce high virus yields.

To complete the manufacturing process, following the upstream process as described, the influenza strains that serve as antigens may undergo extensive down stream processing before the vaccine is formulated into the final product. Downstream processing is not within the scope of this application.

Previously, for influenza vaccine production, the Vero cell line is associated with unsatisfactory virus yields and numerous technical difficulties. Although multiple replication cycles of influenza strains are possible in Vero cell cultures with repeated doses of L-I-tosylamide-2-phenylethyl chloromethyl ketone-treated (TPCK) or TrypZean (a ADCF bovine trypsin recombinant expressed in corn, Sigma-Aldrich Co.) virus yields of most strains in Vero cells are still too low for cost effective vaccine production. Applicants demonstrate, however, that limited passage in Vero cells of wild-type candidates at high multiplicity of infection produce titers satisfactory for virus seed and subsequent virus production eliminating the need for extensive and elaborate procedures like reassortment or reverse genetics.

Historically, ADCF adapted cells have been difficult to synchronize in an ADCF microcarrier culture system. First, ADCF cells are difficult to attach to ADCF microcarriers, then cell distribution tends to be skewed leading to numerous production problems, and finally cells fail to spread eventually falling off the microcarriers. Gelatin-coated microcarriers, therefore, remain a component in the so called ADCF culture platform. Applicants have demonstrated synchronized cell attachment, consistent cell distribution among microcarriers, a good rate of cell spreading, and good cell growth as required for a satisfactory virus infection using ADCF HILLEX® II microcarriers.

Prior to culture initiation, equipment and materials are prepared. Culture vessels can include spinner flasks equipped with impellers with stir plates controlling the speed of the impeller or computer controlled bioreactors equipped with set points for temperature, dissolved oxygen, pH controlled by $CO_2$, acids or bases, impeller rpm ranging from 0 to 60, Culture vessels are configured before sterilizing for culture initiation. HILLEX® II or other ADCF microcarriers are sterilized in DI water or DPBS. Media without phenol red is recommended, but not required, for HILLEX® II.

ADCF adapted Vero cells are expanded from a working cell bank by serial passages in T-flasks, roller bottles, microcarrier cultures or various other platforms until the desired cell counts are achieved for batch production of each of the various strains of influenza virus.

Prior to culture initiation, confluent ADCF adapted cells are removed from the substrate using ADCF-type trypsin forming a single cell suspension which is transferred to the ADCF HILLEX® II culture system.

To remove cells from the substrate, monolayers are rinsed with DPBS twice and or a weak solution of EDTA in DPBS with 10-30 minute incubation periods before cells are dissociated from the substrate using ADCF cell detachment solution such as HYQTASE® (Hyclone Laboratories, Inc.) or TRYPLE® select (Invitrogen Corporation). A satisfactory process step results in a viable, single cell suspension essential for microcarrier culture initiation.

A successful HILLEX® II culture initiation is dependent upon 1) single cell suspension with 92% viability or better, 2) pH management, 3) rpm set at 50-60, 4) culture vessel fitted with a proper impeller to keep the HILLEX® II microcarriers in suspension, 5) optimized temperature range for optimized cell growth, and 6) dissolved oxygen of 5% or higher.

Once the desired cell density is achieved with ADCF media, the cells monolayered on ADCF HILLEX® II microcarriers must be properly maintained for a successful influenza infection process step. The ADCF culture at this stage in the upstream process must be robust to survive the repeated doses of enzyme used to cleave the HA protein necessary for multiple rounds of virus replication in Vero cell cultures. Since the currently available ADCF media are designed explicitly for growth, not maintenance, required media exchanges with ADCF media results in overgrowth causing the cell monolayers to slough off the microcarriers. Applicants demonstrate that maintaining robust cells, not with ADCF growth media, rather with a maintenance-type media, ADCF DMEM without additives except L-glutamate for example, properly maintains confluent, robust cells at a substantially reduced cost for the subsequent influenza virus infection step leading to high virus titers Soon after the cells are 85% confluent to barely contiguous, the ADCF media is replaced with a maintenance media without animal proteins like DMEM supplemented with only L-glutamine. The cells will remain robust in the later exponential phase until the infection step is initiated typically within 2 to 24 hours.

The method of the present invention can be used for wild type influenza virus adaptation to Vero cells and the ADCF upstream process conditions made possible by the unique ADCF properties of HILLEX® II supporting cell attachment, cell spreading, cell growth, robust cell maintenance during Vera cell infection using wild-strain influenza seed virus adapted to Vera cells.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLES

Methods:

General methods in molecular biology: Standard molecular biology techniques known in the art and not specifically described are generally followed as in Sambrook et al., *Molecular Cloning: A Laboratory Manual*, Cold Spring Harbor Laboratory Press, New York (1989), and in Ausubel et al., *Current Protocols in Molecular Biology*, John Wiley and Sons, Baltimore, Md. (1989) and in Perbal, *A Practical Guide to Molecular Cloning*, John Wiley & Sons, New York (1988), and in Watson et al., *Recombinant DNA*, Scientific American Books, New York and in Birren et al. (eds) *Genome Analysis: A Laboratory Manual Series*, Vols. 1-4 Cold Spring Harbor Laboratory Press, New York (1998) and methodology as set forth in U.S. Pat. Nos. 4,666,828; 4,683,202; 4,801,531; 5,192,659 and 5,272,057 and incorporated herein by reference. Polymerase chain reaction (PCR) was carried out generally as in *PCR Protocols: A Guide To Methods And Applications*, Academic Press, San Diego, Calif. (1990). In-situ (In-cell) PCR in combination with Flow Cytometry can be used for detection of cells containing specific DNA and mRNA sequences (Testoni et al., 1996, Blood 87:3822.)

General methods in immunology: Standard methods in immunology known in the art and not specifically described are generally followed as in Stites et al. (eds), Basic and Clinical Immunology (8th Edition), Appleton & Lange, Norwalk, Conn. (1994) and Mishell and Shiigi (eds), Selected Methods in Cellular Immunology, W. H. Freeman and Co., New York (1980).

Antibody Production

Antibody Production: Antibodies may be either monoclonal, polyclonal, or recombinant. Conveniently, the antibodies may be prepared against the immunogen or portion thereof. For example, a synthetic peptide based on the sequence, or prepared recombinantly by cloning techniques or the natural gene product and/or portions thereof may be isolated and used as the immunogen. Immunogens can be used to produce antibodies by standard antibody production technology well known to those skilled in the art as described generally in Harlow and Lane, *Antibodies: A Laboratory Manual*, Cold Spring Harbor Laboratory, Cold Spring Harbor, N.Y., 1988 and Borrebaeck, *Antibody Engineering—A Practical Guide*, W. H. Freeman and Co., 1992. Antibody fragments also can be prepared from the antibodies and include Fab, F(ab')$_2$, and Fv by methods known to those skilled in the art.

For producing polyclonal antibodies, a host, such as a rabbit or goat, is immunized with the immunogen or immunogen fragment, generally with an adjuvant, and if necessary, coupled to a carrier; antibodies to the immunogen are collected from the sera. Further, the polyclonal antibody can be absorbed such that it is monospecific. That is, the sera can be absorbed against related immunogens so that no cross-reactive antibodies remain in the sera, rendering it monospecific.

For producing monoclonal antibodies, the technique involves hyperimmunization of an appropriate donor with the immunogen, generally a mouse, and isolation of splenic antibody producing cells. These cells are fused to a cell having immortality, such as a myeloma cell, to provide a fused cell hybrid that has immortality and secretes the required antibody. The cells are then cultured, in bulk, and the monoclonal antibodies harvested from the culture media for use.

For producing recombinant antibody (see generally Huston et al., 1991; Johnson and Bird, 1991; Mernaugh and Mernaugh, 1995), messenger RNAs from antibody producing B-lymphocytes of animals, or hybridoma, are reverse-transcribed to obtain complimentary DNAs (cDNAs). Antibody cDNA, which can be full or partial length, is amplified and cloned into a phage or a plasmid. The cDNA can be a partial length of heavy and light chain cDNA, separated or connected by a linker. The antibody, or antibody fragment, is expressed using a suitable expression system to obtain recombinant antibody. Antibody cDNA can also be obtained by screening pertinent expression libraries.

The antibody can be bound to a solid support substrate or conjugated with a detectable moiety or be both bound and conjugated as is well known in the art. (For a general discussion of conjugation of fluorescent or enzymatic moieties see Johnstone & Thorpe, *Immunochemistry in Practice*, Blackwell Scientific Publications, Oxford, 1982). The binding of antibodies to a solid support substrate is also well known in the art. (For a general discussion, see Harlow & Lane *Antibodies: A Laboratory Manual*, Cold Spring Harbor Laboratory Publications, New York, 1988 and Borrebaeck, *Antibody Engineering—A Practical Guide*, W.H. Freeman and Co., 1992) The detectable moieties contemplated with the present invention can include, but are not limited to, fluorescent, metallic, enzymatic and radioactive markers such as biotin, gold, ferritin, alkaline phosphatase, b-galactosidase, peroxidase, urease, fluorescein, rhodamine, tritium, $^{14}C$ and iodination.

Delivery of Gene Products/Therapeutics (Compound):

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound made by the steps of the present invention can be administered in various ways. It should be noted that it can be administered as the compound or as pharmaceutically acceptable salt and can be administered alone or as an active ingredient in combination with pharmaceutically acceptable carriers, diluents, adjuvants and vehicles. The compounds can be administered orally, subcutaneously or parenterally including intravenous, intraarterial, intramuscular, intraperitoneally, and intranasal administration as well as intrathecal and infusion techniques. Implants of the compounds are also useful. The patient being treated is a warm-blooded animal and, in particular, mammals including man. The pharmaceutically acceptable carriers, diluents, adjuvants and vehicles as well as implant carriers generally refer to inert, non-toxic solid or liquid fillers, diluents or encapsulating material not reacting with the active ingredients of the invention.

It is noted that humans are treated generally longer than the mice or other experimental animals exemplified herein which treatment has a length proportional to the length of the disease process and drug effectiveness. The doses may be single doses or multiple doses over a period of several days, but single doses are preferred.

The doses may be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various other ingredients, as desired.

A pharmacological formulation of the present invention can be administered to the patient in an injectable formulation containing any compatible carrier, such as various vehicle, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include: U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

A pharmacological formulation of the compound utilized in the present invention can be administered orally to the patient. Conventional methods such as administering the compounds in tablets, suspensions, solutions, emulsions, capsules, powders, syrups and the like are usable. Known techniques that deliver it orally or intravenously and retain the biological activity are preferred.

In one embodiment, the compound of the present invention can be administered initially by intravenous injection to bring blood levels to a suitable level. The patient's levels are then maintained by an oral dosage form, although other forms of administration, dependent upon the patient's condition and as indicated above, can be used. The quantity to be administered can vary for the patient being treated and will vary from about 100 ng/kg of body weight to 100 mg/kg of body weight per day and preferably can be from 1 mg/kg of body weight to 10 mg/kg of body weight per day.

Example 1

To support the Vero-ADCF microcarrier process, satisfactory Vero cell adapted master virus seeds must be prepared.

For conventional, large scale influenza virus production, strains of influenza selected for annual vaccine production are likely configured for seed virus by reassorting the wild-type strain with A/Puerto Rico/8/34 (PR8), a master strain adapted to grow in embryonated eggs for enhanced virus yields. Reassorted viruses are screened for surface antigen, hemagglutinin (HA) and neuraminidase (NA), genes from targeted wild-type strains and structural genes from the PR8 master strain virus. These reassorted influenza viruses are then grown in embryonated eggs to expand viruses used as working seed for production batches.

Preparing Influenza virus seed for the Vero ADCF platform typically involves adaptation to Vero cells to increase titers suitable for master seed.

Govorkova, et. al. reported A/England/1/53 titers of 8.37 $\log_{10}$ TCID$_{50}$/ml only after 20 passages using a low MOI in Vero cells. Considering the time constrains, this protocol is not practical for commercial-scale manufacturing. However, there is demonstrated a practical approach to developing virus seed for influenza production. Five of six recent wild-type influenza virus strains isolated and expanded in embryonated eggs did indeed require adaptation to Vero cells before they were regarded as suitable for the seed virus used to produce consistently high titers. However, only five or less passages were required for these five strains of human influenza virus grown in eggs and serial passaged at a high MOI (1 to 10) in Vero cells over a period of only 12 days; A/Beijing/262/95, A/Moscow/10/99, A/Sydney/05/97, B/Harbin/07/94 and A/New Calcdonia/20/99. Only A/Panama/2007/99 required no multiple passage adaptation. These results indicate the adaptability of human influenza virus strains to Vero cells and the suitability of this method for preparing influenza master seeds used for seasonal manufacturing of influenza virus antigens. Future studies are required to determine the genetic stability of human influenza virus strains using this protocol.

| Influenza Virus Adaptation to Vero Cells $\log_{10} TCID_{50}/ml$ | | | |
|---|---|---|---|
| Strain | Egg | Vero p.1 | Vero p.4 |
| A/Beijing | 8.5 | 0 | 7.6 |
| A/New Caledonia | 8.2 | 0 | 8.1 |
| A/Moscow | 7.5 | 4.8 | 7.8 |
| A/Sydney | 8.0 | 6.3 | 7.5 |
| A/Panama | 7.8 | 7.9 | 8.0 |
| B/Harbin | 7.2 | 0 | 7.4 |

Prior to culture initiation, equipment and materials are prepared: Culture vessels can include spinner flasks equipped with impellers with stir plates controlling the speed of the impeller or computer controlled bioreactors equipped with set points for temperature, dissolved oxygen, pH controlled by $CO_2$, acids or bases, impeller rpm ranging from 0 to 60, Culture vessels are configured before sterilizing for culture initiation. HILLEX® II or other ADCF microcarriers are sterilized in DI water or DPBS. Media without phenol red is recommended, but not required, for HILLEX® II.

ADCF adapted Vero cells are expanded from a working cell bank by serial passages in T-flasks, roller bottles, microcarrier cultures or various other platforms until the desired cell counts are achieved for batch production of each of the various strains of influenza virus.

Prior to culture initiation, confluent ADCF adapted cells are removed from the substrate using ADCF-type trypsin forming a single cell suspension which is transferred to the ADCF HILLEX® II culture system.

To remove cells from the substrate, monolayers are rinsed with DPBS twice and or a weak solution of EDTA in DPBS with 10-30 minute incubation periods before cells are dissociated from the substrate using ADCF cell detachment solution such as HYQTASE® (Hyclone Laboratories, Inc.) or TRYPLE® select (Invitrogen Corporation). A satisfactory process step results in a viable, single cell suspension essential for microcarrier culture initiation.

A successful HILLEX® II microcarrier culture initiation is dependent upon 1) single cell suspension with 92% viability or better, 2) pH management, 3) rpm set at 50-60, 4) culture vessel fitted with a proper impeller to keep the HILLEX® II microcarriers in suspension, 5) optimized temperature range for cell growth data, and 6) dissolved oxygen of 5% or higher. For example, HILLEX® II microcarriers are transferred to the culture vessel in ½ to ¾ volume of the total culture volume at least 1 hour before cell suspension is added-1300 cm.sup.2 to 2600 cm.sup.2 or greater surface area per 200 mls of ADCF media. Single cell suspension is transferred to the culture vessel with the impeller running at a rate of 50-60 rpm, the pH at 7.5-7.6, and temperature at 37.degree. C. (Seeding density is 10 to 20 cells per microcarrier added to the culture depending on many factors including manufacturing schedule.) For synchronized, evenly distributed cell attachment to HILLEX® II, the impeller is on until cell attachment is achieved, typically within 30 minutes as shown in FIG. 1.

Conditions for Cell Spreading on HILLEX® II Microcarriers.

Once 90% of the cells have attached to the microcarriers, culture conditions for the cell attachment phase are imposed. Set point for pH can be adjusted to 7.2-7.4. Intermittent stirring cycle is initiated for a period of up to 24 hours. For example—3 minutes on at 50-60 rpm and 30 minutes off. The current experience is for 3 hours to 24 hours depending on the schedule and, indeed, the rate of spreading which is based on the condition of the cells at the time the culture was initiated. (Ref. cell control)

Once the cells have spread, the impeller is turned on at a constant speed of 50-60 rpm, for example. (rpm is dependent on the configuration of the impeller assembly within the stir vessel and is determined empirically.) FIG. 2 shows Vero cells spreading (white) on HILLEX® within 24 hours during intermittent stirring. FIG. 3 shows Vero cells growing (white) on HILLEX® after 72 hours in culture.

Conditions for ADCF Vero Cell Growth on HILLEX® II Microcarriers (24 hrs) pH=7.2 to 7.5. rpm=50-60. d0=10 to 30%. Temperature=37C. Add media to final desired culture volume. Exchange media as required based on empirical growth curve data including the concentration of cells growing on microcarriers per volume of media. For example—½ media exchange on day 3 and on day 4 before the cells are confluent on the HILLEX® II. FIG. 4 shows confluent Vero ADCF cells on HILLEX® after 4 days in culture. Insert Vero ADCF confluent 1 picture. FIG. 5 shows growth curve; x axis number of cells and y axis hours in culture.

Conditions for ADCF Vero Cell Maintenance

Once the desired cell density (cells/cm2) is achieved with ADCF media, the cells monolayered on ADCF HILLEX® II microcarriers must be properly maintained for a successful influenza infection process step. The ADCF culture at this stage in the upstream process must be robust to survive the repeated doses of enzyme used to cleave the HA protein necessary for multiple rounds of virus replication in Vero cell cultures. Since the currently available ADCF media are designed explicitly for growth, not maintenance, required media exchanges with ADCF media results in overgrowth causing the cell monolayers to slough off the microcarriers.

Soon after the cells have reached confluence, the ADCF media is replaced with a maintenance media without animal proteins like DMEM supplemented with perhaps only L-glutamine. The cells will remain robust in the late exponential phase until the infection step is initiated typically within 12 to 24 hours.

Conditions for ADCF Vero Cell Influenza Infection

Cell density (cells/cm2) is an important function of influenza cell infection efficiency and yields. Cells on the microcarriers are rinsed by exchanging the media with maintenance media. Depending on the influenza virus two rinses may be required based on influenza strain growth curve data. Thoroughly rinsing is required to eliminate residual protein in the culture that tends to inactivate the trypsin which is required for proper infection. For the infection, fresh maintenance media is added supplemented with L-glutamate ½ to one full volume. Master virus seed is added at a moi of 0.01 to 0.0001 depending on development results of each strain of influenza. ADCF trypsin is added immediately after the seed virus at the proper concentration to cleave the HA protein. pH=7.4 to 7.6, Temperature=depends on strain, d0=5% to 30%, rpm=50-60.

Harvest

Time of harvest depends on type of antigen desired; high viability virus or total antigen including viable and non viable virus. Supernatant is harvested through a biofilter leaving the microcarriers in the vessel or simply by allowing microcarriers to settle before transferring virus-laden fluids to a harvest vessel.

Figure 1:
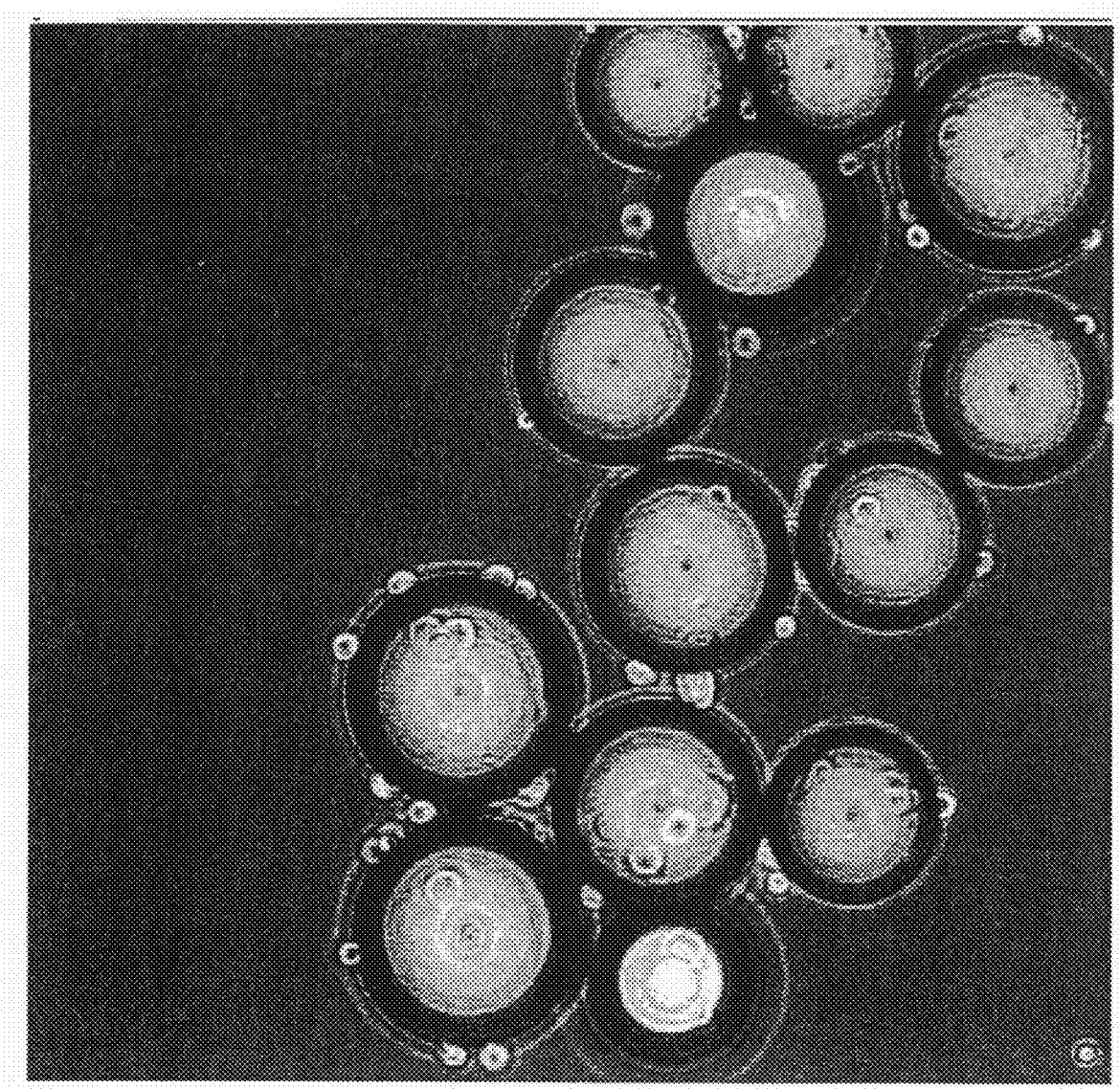
Figure 2:
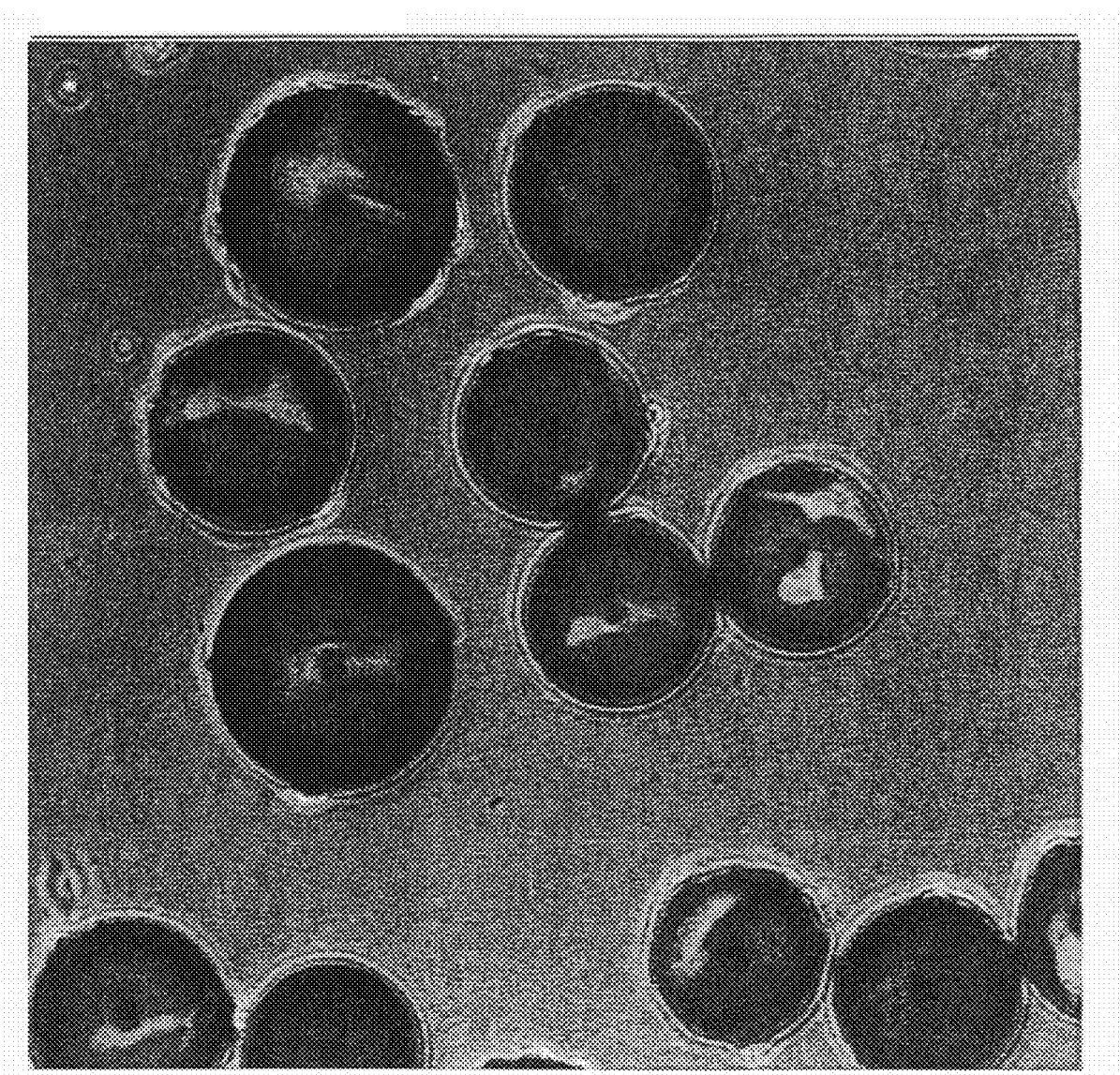
Figure 3:
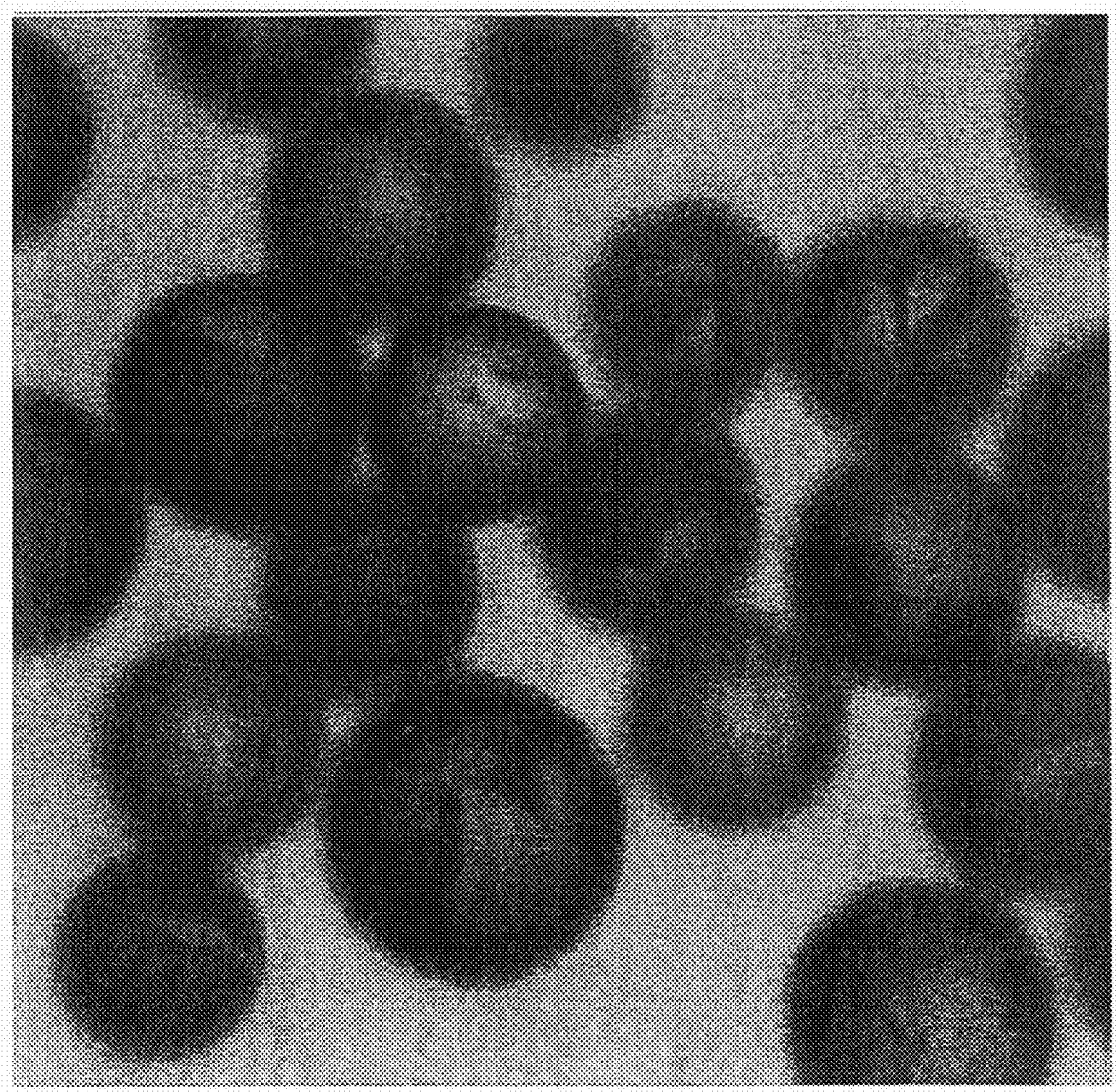
Figure 4:
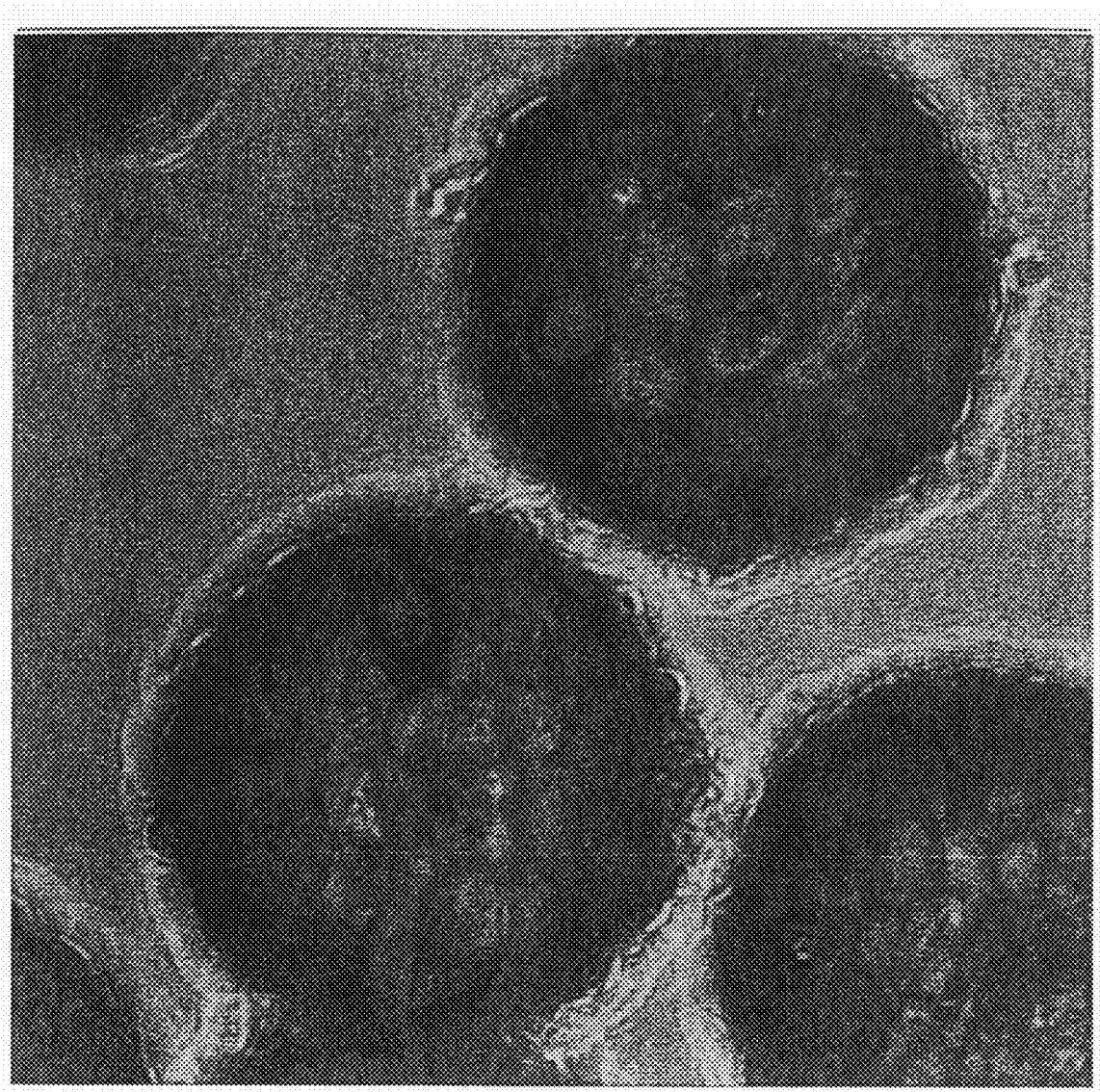
Figure 5:
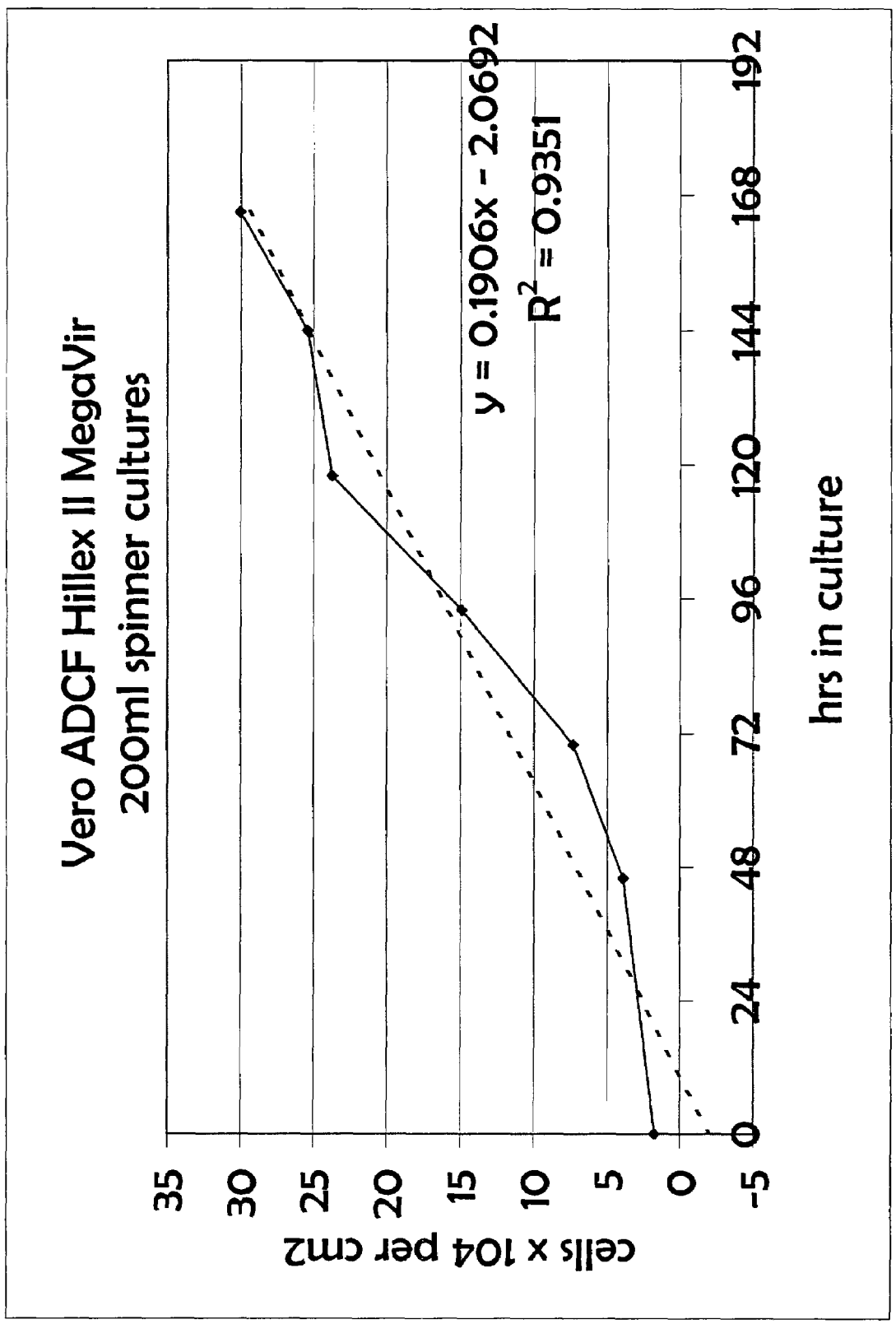
Figure 6:
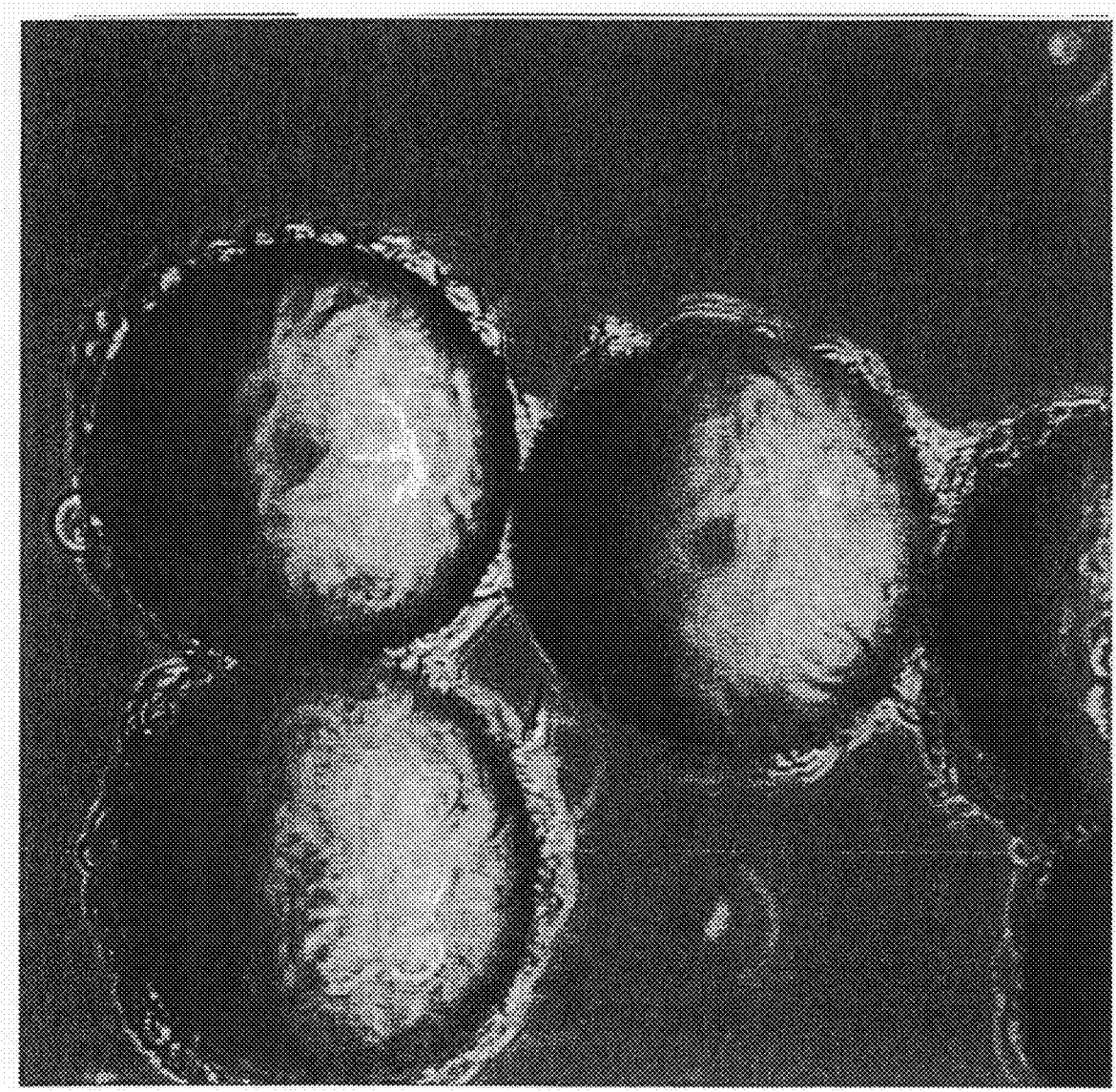
FIG. 6 shows cells properly maintained with ADCF DMEM prior to infection. Insert Vero ADCF maintained DMEM 020 or 013.
Figure 6:
Figure 7:
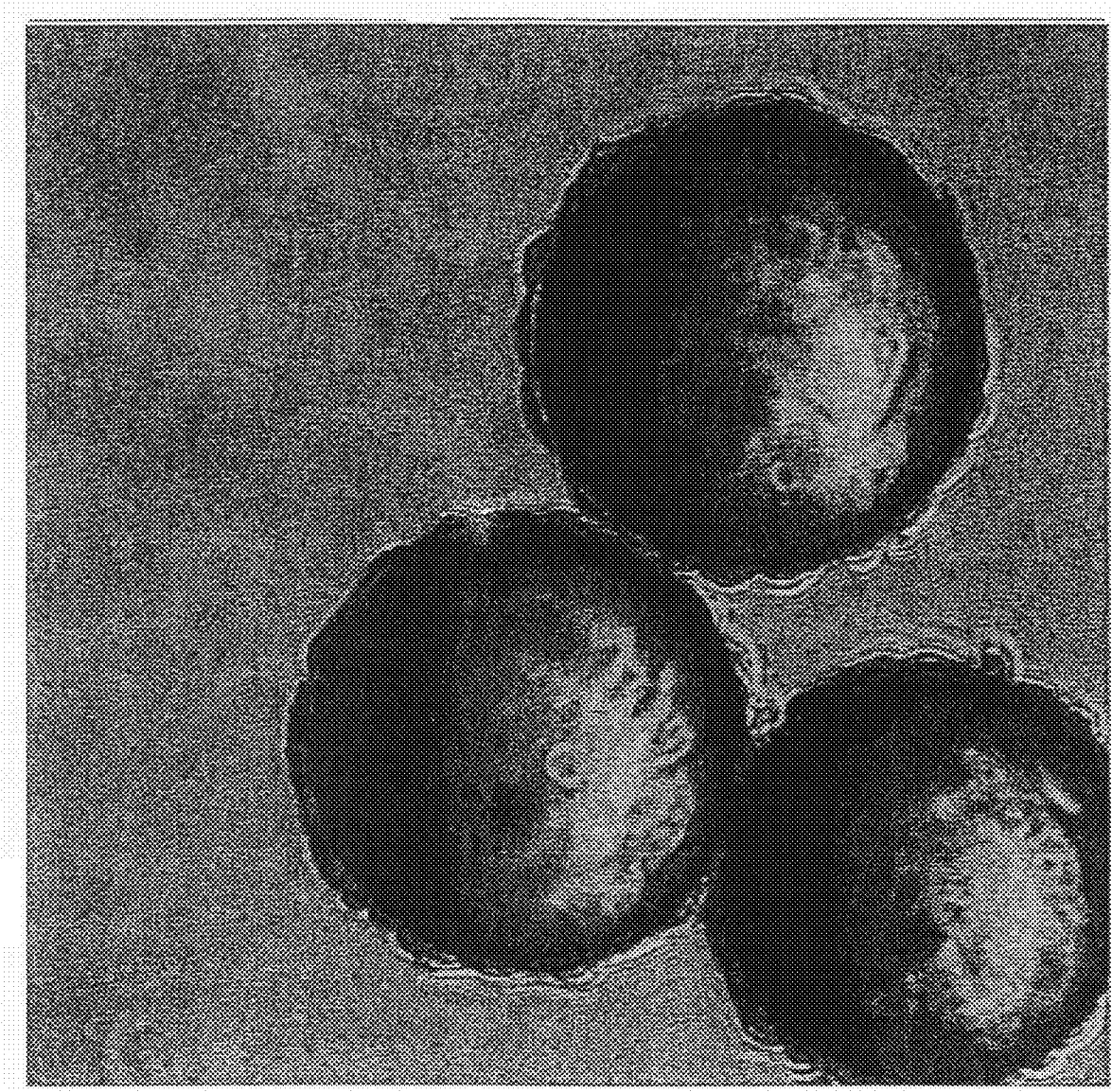
FIG. 7 shows cells improperly maintained with ADCF growth media resulting in cells slough off microcarriers.
Figure 8:
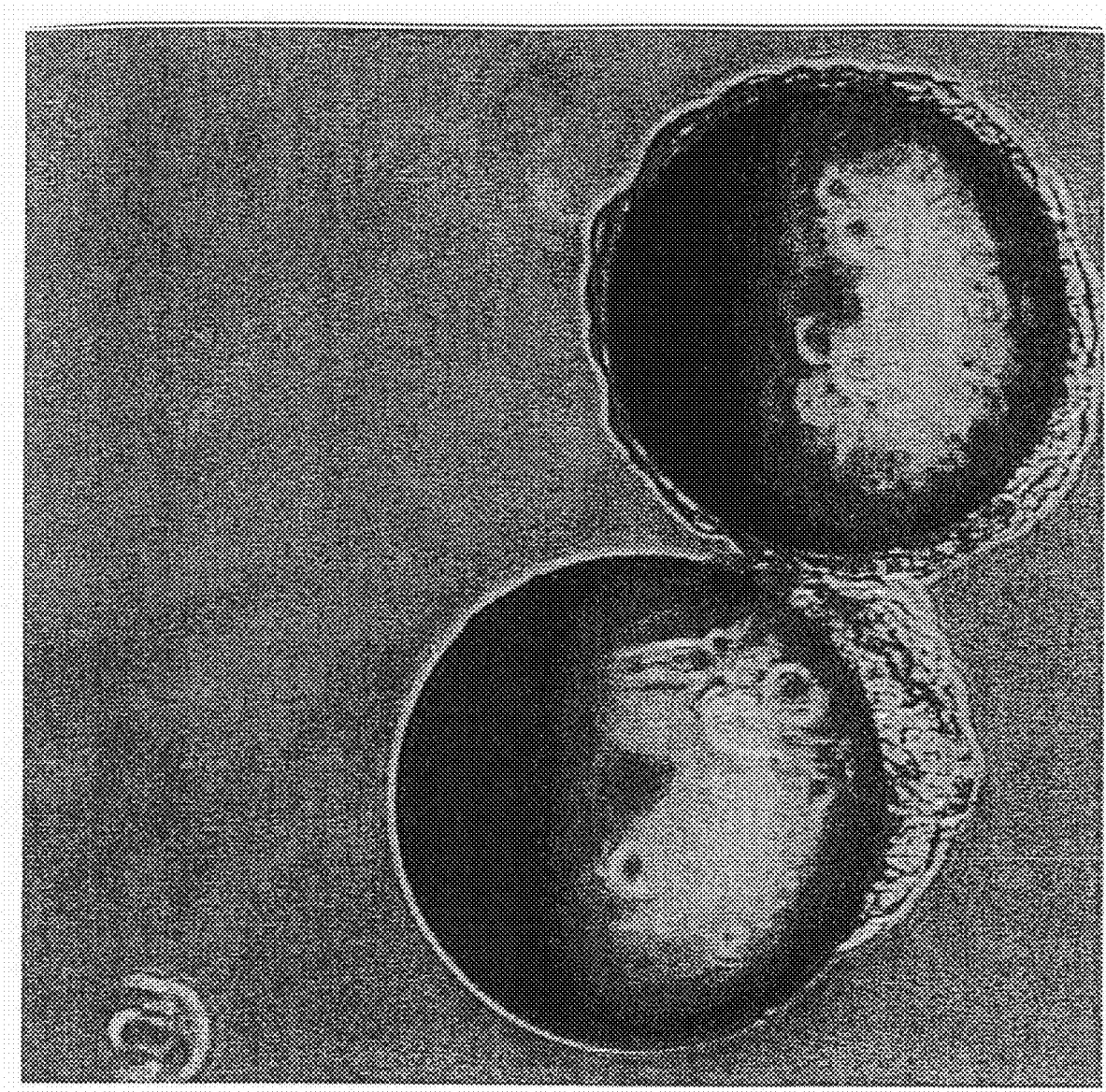

A Comparison of A/Panama H.sub.3N.sub.2 Harvest Titer FIG. 8 shows the following information: TABLE-US-00002 Embryonated eggs log.sub.107.8 TDIC/ml (conventional) Vero serum containing cultures 7.9 (HILLEX® spinner cultures) Vero ADCF system 8.0 (HILLEX® spinner cultures)

Throughout this application, author and year, and patents, by number, reference various publications, including United States patents. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology that has been used is intended to be in the nature of words of description rather than of limitation.

Obviously, many modifications and variations of the present invention are possible in light of the above teachings. It is, therefore, to be understood that within the scope of the described invention, the invention may be practiced otherwise than as specifically described.

REFERENCES

Brands R., et. al. Influvac, A safe Madin Darby Canine Kidney (MDCK) cell culture-based influenza vaccine. Dev. Biol. Standards 98:93-100, 1999.

Bull. World Health Organ. 73:431-435, 1995. Cell culture as a substrate for the production of influenza vaccines; Memorandum from a WHO meeting.

Govorkova E. A. et. al. Growth and immunogenicity of influenza viruses cultivated in Vero or MDCK cells and in embryonated eggs. Dev. Biol. Standards 98:39-51, 1999.

Govorkova, E. A. et. al. Replication of Influenza A Viruses in a Green Monkey Kidney Continuous Cell Line (Vero). J Infect Dis 1995; 250-253.

Kisstner O., et. al. Development of a Vero-derived influenza whole virus vaccine. Dev. Biol. Standards 98:101-110, 1999.

Kaverin N. V., et. al. Impairment of multicycle influenza virus growth in Vero (WHO) cells by loss of trypsin activity. J. Virol. 69:2700-2703, 1995.

Katz J. M., et. al. Efficacy of inactivated influenza A virus (H3N2) vaccines grown in mammalian cells or embryonated eggs. J. Infect. Dis. 160:191-198, 1989.

Merten O. W., et. al. Production of influenza virus in serum-free mammalian cell cultures. Dev. Biol. Standards 98:23-27, 1999.

Ozaki, H., et. al. Generation of high-yielding influenza A viruses in African Monkey Kidney (Vero) cell by reverse genetics. J. Virol. 2004 p. 1851-1857.

Wood J. M., Standardization of inactivated vaccine. Textbook of Influenza, p 337, Blackwell Science Ltd., London, 1998.

Burke and Olson, "Preparation of Clone Libraries in Yeast Artificial-Chromosome Vectors" in *Methods in Enzymology*, Vol. 194, "Guide to Yeast Genetics and Molecular Biology", eds. C. Guthrie and G. Fink, Academic Press, Inc., Chap. 17, pp. 251-270 (1991).

Capecchi, "Altering the genome by homologous recombination" *Science* 244:1288-1292 (1989).

Davies et al., "Targeted alterations in yeast artificial chromosomes for inter-species gene transfer", *Nucleic Acids Research*, Vol. 20, No. 11, pp. 2693-2698 (1992).

Dickinson et al., "High frequency gene targeting using insertional vectors", *Human Molecular Genetics*, Vol. 2, No. 8, pp. 1299-1302 (1993).

Duff and Lincoln, "Insertion of a pathogenic mutation into a yeast artificial chromosome containing the human APP gene and expression in ES cells", *Research Advances in Alzheimer's Disease and Related Disorders*, 1995.

Huxley et al., "The human HPRT gene on a yeast artificial chromosome is functional when transferred to mouse cells by cell fusion", *Genomics*, 9:742-750 (1991).

Jakobovits et al., "Germ-line transmission and expression of a human-derived yeast artificial chromosome", *Nature*, Vol. 362, pp. 255-261 (1993).

Lamb et al., "Introduction and expression of the 400 kilobase precursor amyloid protein gene in transgenic mice", *Nature Genetics*, Vol. 5, pp. 22-29 (1993).

Pearson and Choi, *Expression of the human b-amyloid precursor protein gene from a yeast artificial chromosome in transgenic mice*. Proc. Natl. Acad. Sci. USA, 1993. 90:10578-82.

Rothstein, "Targeting, disruption, replacement, and allele rescue: integrative DNA transformation in yeast" in *Methods in Enzymology*, Vol. 194, "Guide to Yeast Genetics and Molecular Biology", eds. C. Guthrie and G. Fink, Academic Press, Inc., Chap. 19, pp. 281-301 (1991).

Schedl et al., "A yeast artificial chromosome covering the tyrosinase gene confers copy number-dependent expression in transgenic mice", *Nature*, Vol. 362, pp. 258-261 (1993).

Strauss et al., "Germ line transmission of a yeast artificial chromosome spanning the murine $a_1$ (I) collagen locus", *Science*, Vol. 259, pp. 1904-1907 (1993).

Gilboa, E, Eglitis, M A, Kantoff, P W, Anderson, W F: Transfer and expression of cloned genes using retroviral vectors. BioTechniques 4(6):504-512, 1986.

Cregg J M, Vedvick T S, Raschke W C: Recent Advances in the Expression of Foreign Genes in *Pichia pastoris*, Bio/Technology 11:905-910, 1993

Culver, 1998. Site-Directed recombination for repair of mutations in the human ADA gene. (Abstract) Antisense DNA & RNA based therapeutics, February, 1998, Coronado, C A.

Huston et al., 1991 "Protein engineering of single-chain Fv analogs and fusion proteins" in Methods in Enzymology (J J Langone, ed.; Academic Press, New York, N.Y.) 203:46-88.

Johnson and Bird, 1991 "Construction of single-chain Fvb derivatives of monoclonal antibodies and their production in *Escherichia coli* in Methods in Enzymology (J J Langone, ed.; Academic Press, New York, N.Y.) 203:88-99.

Mernaugh and Mernaugh, 1995 "An overview of phage-displayed recombinant antibodies" in Molecular Methods In Plant Pathology (R P Singh and U S Singh, eds.; CRC Press Inc., Boca Raton, Fla.) pp. 359-365.

U.S. PATENT DOCUMENTS

U.S. Pat. No. 6,214,618 B1 4/2001 Hillegas et al.

We claim:

1. A method of making an influenza vaccine using animal derived component free (ADCF) cell culture technology, including the steps of: attaching ADCF-adapted cells to a microcarrier including attachment means for attaching filipodia of the cells and suspending the microcarrier by an impeller turning at a constant speed of 50 to 60 rpm, the microcarrier being in a culture; growing the cells in ADCF maintenance media; infecting the cells with influenza vaccine media; producing influenza virus within the cells; and harvesting the influenza virus.

2. The method of claim 1, wherein the attaching step is further defined as removing ADCF-adapted cells from substrate using ADCF trypsin resulting in a single cell suspension, adding the single cell suspension to the culture, uniformly attaching the cells to the microcarrier, and spreading the cells to the microcarrier.

3. The method of claim 2, wherein the spreading step is further defined as setting the pH at 7.2-7.4, setting an intermittent stirring cycle for up to 24 hours.

4. The method of claim 1, wherein the producing step is further defined as timing cell infection relative to cell seeding density on the microcarrier and growth phase of the cell to synergistically produce high virus yield.

5. The method of claim 1, wherein the harvesting step is further defined as harvesting the supernatant to collect the virus.

6. The method of claim 2, further including the step of transferring the microcarrier to the culture at least one hour before adding the single cell suspension to the culture.

7. The method of claim 6, wherein the culture includes an impeller running at a rate of 50 to 60 rpm, with a pH at 7.5 to 7.6, and temperature at 37 degrees C.

8. The method of claim 7, wherein the impeller runs for at least 30 minutes to allow for cell attachment to the microcarrier.

9. The method of claim 1, wherein the attachment means of the microcarrier beads is a micro-porous surface.

10. The method of claim 9, wherein the microcarrier beads have a density of 1.04 to 1.1 g/cc.

11. The method of claim 9, wherein the microcarrier beads have a diameter of 75 to 225 micrometers.

12. The method of claim 9, wherein the microcarrier beads are made of a material chosen from the group consisting of glass, polystyrene plastic, acrylamide, dextran, solid collagen, porous collagen, porcine collagen, cellulose, and liquid fluorocarbon.

13. The method of claim 9, wherein the microcarrier beads are made of a material chosen from the group consisting of porcine collagen coated polystyrene and glass-coated polystyrene.

14. The method of claim 9, wherein the microcarrier beads include at least one adhesive peptide attached to a surface of the microcarrier bead through covalent or noncovalent linkages.

15. The method of claim 9, wherein the microcarrier beads include a coating chosen from the group consisting of porcine, collagen, bovine collagen, human collagen, ProNectin F, recombinant fibronectin, and any other suitable natural or synthetic peptide.

16. The method of claim 1, wherein the vaccine media is Vero cell adapted influenza virus working seeds.

17. The method of claim 1, wherein the ADCF-adapted cells are Vero or Madin-Darby Canine Kidney (MDCK) cells.

* * * * *